United States Patent [19]

Lewis et al.

[11] Patent Number: 5,521,082
[45] Date of Patent: May 28, 1996

[54] NOVEL PROCESS FOR PURIFICATION OF HEPATITIS A VIRIONS

[75] Inventors: John A. Lewis, West Chester; Marcy E. Armstrong, Schwenksville; Emilio A. Emini, Paoli, all of Pa.

[73] Assignee: Merck & Co., Inc., Rahway, N.J.

[21] Appl. No.: 967,920

[22] Filed: Oct. 28, 1992

Related U.S. Application Data

[63] Continuation of Ser. No. 783,717, Oct. 25, 1991, abandoned, which is a continuation of Ser. No. 547,409, Jul. 2, 1990, abandoned, which is a continuation of Ser. No. 82,720, Aug. 6, 1987, abandoned.

[51] Int. Cl.[6] .............................. C12N 7/00; C12N 7/02; C12N 7/04; C12N 7/08
[52] U.S. Cl. .................. 435/235.1; 435/236; 435/239
[58] Field of Search ............................ 435/235.1, 239, 435/236, 6, 7, 7.1, 235, 23.9, 23.6

[56] References Cited

U.S. PATENT DOCUMENTS

| | | | |
|---|---|---|---|
| 3,919,044 | 11/1975 | Melnick et al. | 435/239 |
| 3,994,870 | 11/1976 | Neurath | 530/380 |
| 4,164,566 | 8/1979 | Provost et al. | 424/89 |
| 4,614,793 | 9/1986 | Hughes et al. | 530/350 |
| 4,683,294 | 7/1987 | Van Wijnendaele et al. | 530/371 |
| 4,894,228 | 1/1990 | Purcell et al. | 14/894 |

FOREIGN PATENT DOCUMENTS

| | | |
|---|---|---|
| 2398504 | 2/1979 | European Pat. Off. . |
| 0522291 | 1/1993 | European Pat. Off. . |
| 2398504 | 2/1979 | France . |

OTHER PUBLICATIONS

Maniatis et al Molecular Cloning CSH (1982) pp. 80–81, 458–459.

Wheeler, C. N., et al., Journal of Virology, vol. 58, pp. 307–313, 1986 (May).

Crance, J. M., et al., C. R. Seances Acad. Sci. Paris, Serie III, vol. 293, pp. 693–696, 1981 (Dec.).

Welling, G. W., et al., Journal of Chromatography, vol. 297, pp. 101–109, 1984.

J. A. Lewis et al, Proceedings of the International Symposium on Viral Hepatitis and Liver Disease, pp. 94–97 (1990).

R. Najarian et al., Proc. Natl. Acad. Sci. 82: pp. 2627–2631 (1985).

R. J. Gerety (ed.) Hepatitis A–Academic Press pp. 263–276 (1984).

S. M. Feinstone, Progress in Liver Diseases 8: 299–310 (1986).

A. M. Mijch et al., Seminars in Liver Diseases 6: 42–45 (1986).

C. L. Hornbeck et al., Intervirology 6:309–314 (1976).

S. A. Locarnini et al., Intervirology 10: 300–308 (1978).

G. Siegel et al., J. Virol. 26: 40–47 (1978).

G. Siegl et al., J. Gen. Virol. 57: 331–341 (1981).

G. Siegl et al., Intervirology 22: 218–226 (1984).

J. V. Hughes et al., J. Virol. 52: 465–473 (1984).

C. M. Wheeler et al., J. Virol. 58: 307–313 (1986).

J. R. Ticehurst, Seminars in Liver Disease 6: 46–55 (1986).

P. J. Provost et al., Proc. Soc. Exp. Biol. Med. 106: 213–221 (1979).

P. J. Provost et al., J. Med. Virol. 19: 23–31 (1986).

P. J. Provost et al., Proc. Soc. Exp. Biol. Med. 170: 8–14 (1982).

P. J. Provost et al., J. Med. Virol. 20: 165–175 (1986).

(List continued on next page.)

*Primary Examiner*—W. Gary Jones
*Assistant Examiner*—Paul B. Tran
*Attorney, Agent, or Firm*—Joanne M. Glesser; Jack L. Tribble

[57] ABSTRACT

New methods for purifying Hepatitis A virus (HAV) are to commercial scale-up and manufacture of specific HAV vaccines, including formalin-inactivated HAV and attenuated HAV.

7 Claims, 1 Drawing Sheet

OTHER PUBLICATIONS

I. M. Kerr et al., J. of Virology 9: 559–561 (1972).

R. R. Rueckert et al., Meth. in Enzymology 78:315–325 (1976).

P. J. Provost et al., 1987 oral presentation given at International Symposium on Viral Hep. and Liver Disease, London, May 26–28 (1987).

Hilleman et al., Hep. A. and B. Vaccines, 34: 385–397 (1982).

Wheeler et al., J. CLin. Microbial; 23: pp. 434–440 (1986).

J. A. Lewis et al., Proceedings of the International Symposium on Viral Hepatitis and Liver Disease, pp. 94–97 (1990).

Luria, et al., General Virol. Wiley & Sons p. 36–53 (1978).

Davis et al., Microbiology, 3rd ed., Harper & Row pp. 1218–1219 (1980).

Philipson, Methods in Virol., vol. 11, pp. 235–244 (1967).

NOVEL PROCESS FOR PURIFICATION OF HEPATITIS A VIRIONS

This is a continuation of application Ser. No. 07/783,717, filed Oct. 25, 1991, now abandoned, which is a continuation of application Ser. No. 07/547,409, filed Jul. 2, 1990, now abandoned, which is a continuation of application Ser. No. 07/082,720, filed Aug. 6, 1987, now abandoned.

BACKGROUND OF THE INVENTION

Hepatitis A virus (HAV) is a morphologically, biochemically, and immunologically distinct picornavirus that is the etiological agent of infectious hepatitis in humans. Like other picornaviruses, HAV contains a single-stranded, positive-sense, infectious RNA genome. Four major capsid proteins have been described, VP1 (32–33 Kilodaltons or KDa), VP2 (26–29 KDa), VP3 (22–27 KDa) and VP4 (10–14 KDa). HAV has now been cloned and sequenced, e.g., Najarian, R. et al. Proc. Natl. Acad. Sci. 82, 2627 (1985). For recent reviews, see, for example, Gerety, R. J. (ed.) Hepatitis A Academic Press 1984; Feinstone, S. M. Progress in Liver Diseases, 8, 299 (1986); and Mijch, A. M. et al. Seminars in Liver Diseases 6, 42 (1986).

Various methods have been worked out to partially purify HAV virions for the purposes of study and initial characterization. See, for example, Hornbeck, C. L. et al., Interviroloy 6; 309–314 (1975); Locarnini, S. A. et al., Intervirology 10; 300–308 (1978); Siegl, G. et al., J. Virol. 26, 40–47 (1978); Siegl, G. et al., J. Gen. Virol. 57, 331–341 (1981); Siegl, G. et al., Intervirology 22, 218 (1984); Hughes, J. V. et al., J. Virol. 52, 465 (1984); and Wheeler, C. M. et al., J. Virol, 58, 307 (1986). Each of these methods employs one or more steps that are likely to prevent approval by the Food and Drug Administration for the purposes of testing and then selling a safe vaccine against HAV. For example, detergents and/or exogenous enzymes are commonly used. Furthermore, all of these methods employ unwieldy, impractical and excessively expensive steps, such as sucrose gradient centrifugation or CsCl-density gradient centrifugation.

Applicants have discovered methods of obtaining very pure HAV without the use of detergents or exogenous enzymes. Furthermore, the methods disclosed herein can be readily scaled up to commercial production. In addition, applicants have succeeded in adapting these methods to MRC-5 host cells, which are certified by the Food and Drug Administration for human vaccine production.

BRIEF DESCRIPTION OF THE INVENTION

Methods of substantially purifying Hepatitis A virus (HAV) are disclosed, comprising the steps of:

(a) growing and harvesting cells infected with HAV;

(b) lysing the harvested cells by sonication;

(c) extracting the lysate, and retaining the aqueous phase;

(d) concentrating the aqueous phase with a water soluble synthetic polymer effective to precipitate HAV;

(e) extracting the precipitated HAV and retaining the aqueous phase;

(f) subjecting the aqueous phase to ion exchange chromatography;

(g) gel filtering fractions containing HAV, yielding substantially purified HAV. These processes are amendable to commercial scale up and are likely candidates for the commercial production of FDA-approved, inactivated HAV as well as attenuated HAV, for vaccination purposes.

DETAILED DESCRIPTION OF THE INVENTION

Figure 1:
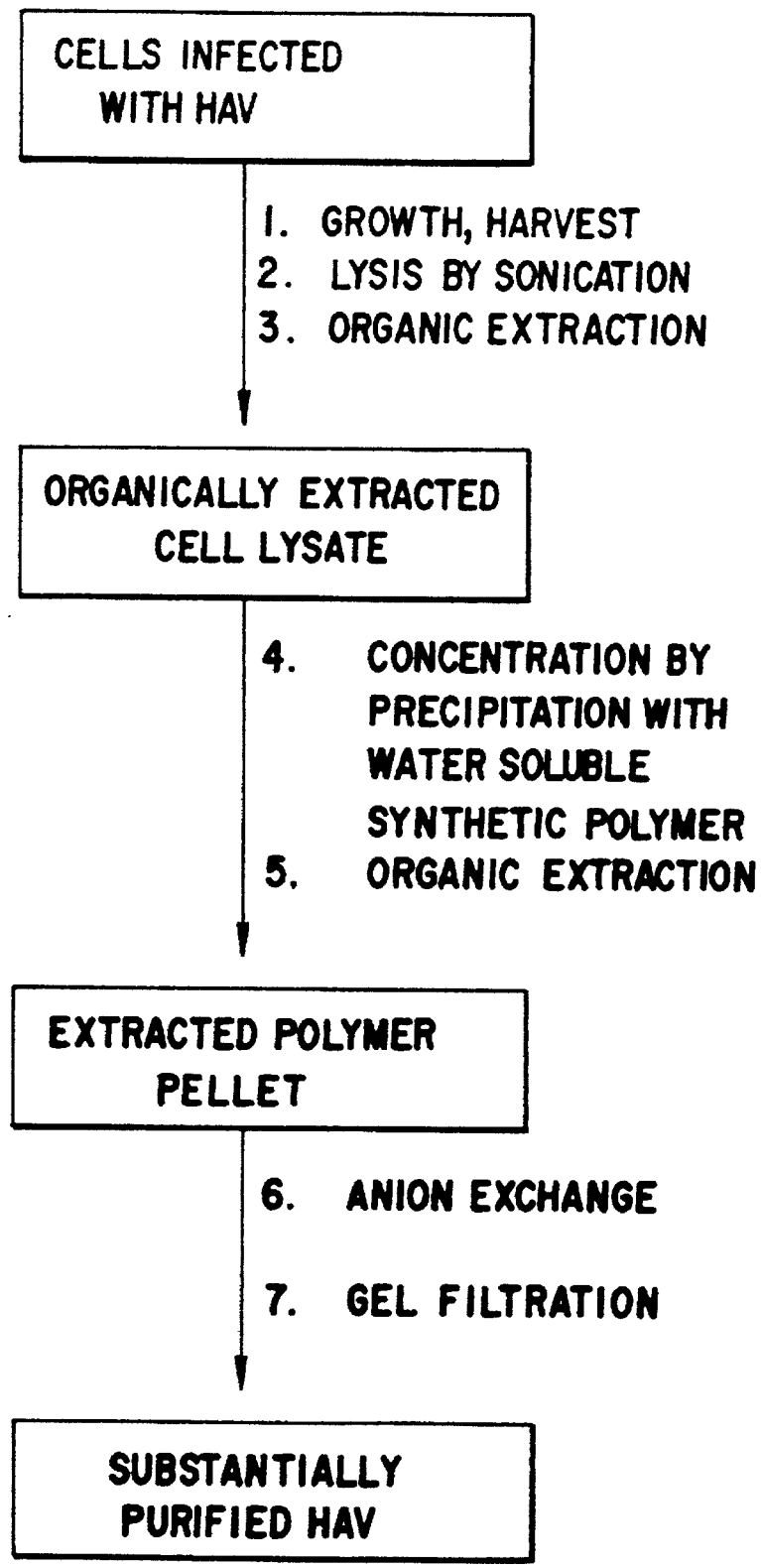

The commercially adaptable purification processes of the present invention encompass the purification of any Hepatitis A virus, attenuated or not, in any cell line or culture susceptible to infection by Hepatitis A virus. The F strain of the CR-326 isolate propagated in MRC-5 cells was used in this invention for merely illustrative purposes, and it happens to be an attenuated strain. Other strains and/or serotypes are encompassed by this invention, including HAV strains that can be attenuated by conventional techniques. Other cell lines include Vero, FL, WI-38 and FRhK6 cells. These and other systems for HAV propagation in cell cultures are discussed in Gerety, R. J. "Active Immunization Against Hepatitis A," in Gerety, R. J. (ed.) Hepatitis A Academic Press 1984, pp. 263–276; and Ticehurst, J. R. Seminars in Liver Disease 6, 46–55 (1986). In principle, any cell line such as any human diploid fibroblast cell line can serve as a host cell provided that it is susceptible to HAV infection. The preferred cell line is MRC-5.

In the description that follows, the number of a paragraph corresponds to the step number of FIG. 1.

1. HAV-infected cells are grown and harvested by any one or more of a variety of conventional techniques. Growth conditions, including the selection of media, depend on the requirements of the cell line employed. For MRC-5 cells, attachment to a substratum is necessary, so that the scraping of cells or trypsinization is a requirement for harvesting. Other cell types useful for the purposes of this invention include those capable of growing in suspension. Suspension cell cultures are normally centrifuged to pellet the cells.

2. After growth and harvest, the HAV-infected cells are lysed by any one or more of a variety of techniques, including but not limited to exposure to hypotonic buffer, vortexing, freeze-thaw cycling, and sonication. Applicants have found that sonication is required for lysis of HAV-infected MRC-5 cells, resulting in efficient release of virions from the cell. (Any release of HAV virions from a disrupted host cell is hereinafter "lysis".) It is thought that sonication efficiently releases HAV virions from its subcellular pseudocrystalline state within the cell. It will be understood that, in addition to sonication, many combinations with hypotonic lysis, vortexing or freeze-thaw cycling can be used for the purposes of proper and effective lysis of cells. Applicants most prefer the following steps in lysing HAV infected MRC-5 cells:

(a) thawing previously frozen, harvested cells in tubes by the addition of lysis buffer (10 mM Tris-HCl pH 7.5, 10 mM NaCl, 1.5 mM $MgCl_2$);

(b) vigorously vortexing (10–15 seconds at setting 10 in a Vortex-Genie);

(c) freeze-thawing one or more times by successive exposure each time to an ethanol-dry ice bath and a 37° C. water bath; and (d) sonicating one or more times for 30 seconds at the maximum wattage output of a cup horn sonicator with a circulating ice water bath (Branson Sonifier Cell Disrupter 185 and Ultrasonics cup horn), yielding a sonicate.

3. After lysis, HAV-infected cells, now a lysed suspension, or sonicate, are diluted with buffer and then subjected to organic extraction. Such extraction removes, among other contaminants, lipid and lipid-like substances. Accordingly, the sonicate is diluted with any one of a variety of buffers, including phosphate buffered saline, Tris, carbonate, bicarbonate or acetate buffers. Since HAV virions are probably acid stable, buffers in an acid pH range are also feasible substitutes. Applicants have discovered that the presence of $MgCl_2$ in the buffer substantially lowers virion yields. The most preferable buffer is TNE (10 mM Tris-HCl pH 7.5, 150 mM NaCl, 1 mM EDTA).

Sonicates diluted with buffer are then extracted by the addition of a mixture of a halogenated lower alkane, such as methylene chloride, and an antifoaming agent, such as isoamyl alcohol. The volume-to-volume ratio of halogenated lower alkane to antifoaming agent is between about 15:1 and about 50:1, preferably between about 20:1 and 30:1. Applicants have found that methylene chloride is superior to chloroform at this stage. HAV virions remain in the aqueous phase and interface.

Most preferably, the sonicate is organically extracted by the addition of an equal volume of methylene chloride: isoamyl alcohol (24:1, v/v) with vortexing for 1 minute and is centrifuged at 3,000 rpm for 10 minutes at 20° C. in an IEC centrifuge (~3,000 g) to achieve phase separation. The aqueous phase is reserved, the organic phase discarded and the interface is reextracted, with a volume of TNE buffer equal to one third of the original sample volume, by vortexing and centrifugation as before. The two aqueous phases are pooled and the volume measured, yielding Hepatitis A virus in organically extracted cell lysates.

4. The next step involves concentration with a water-soluble synthetic polymer effective to precipitate proteins. Applicants prefer to concentrate the organically extracted cell lysates with polyethylene glycol (PEG) having a molecular weight of between about 2,000 daltons and about 12,000 daltons. Typically, NaCl is added to the lysate to a final concentration of between about 150 mM and about 500 mM, then the PEG is added to a final concentration of between about 2% (w/v) and about 10% (w/v). It is most preferable to adjust organically extracted cell lysates to about 500 mM NaCl, then make the lysate about 4% (w/v) in PEG (MW~8000 daltons). Precipitation having occurred, the resulting 4% PEG lysates are centrifuged, the supernatant is discarded and the PEG pellet resuspended for further processing. The resuspended PEG pellet is preferably sonicated before the second organic extraction, described as follows. The product of step 4 is resuspended, sonicated PEG pellet.

5. Resuspended, sonicated PEG pellet is extracted by the addition of a mixture of a halogenated lower alkane, such as chloroform, and an antifoaming agent, such as isoamyl alcohol. The volume-to-volume ratio of halogenated lower alkane to antifoaming agent is between about 15:1 and about 50:1, preferably between about 20:1 and 30:1. Applicants have unexpectedly discovered that this second organic extraction substantially enhances purity of the final HAV product. Futhermore, in contrast to the first organic extraction (see paragraphs corresponding to step 3), applicants have found in the second organic extraction that chloroform is superior to methylene chloride.

Most preferably, the steps of the second extraction are carried out as follows:

The sonicated, resuspended precipitate is rotated at 200 rpm on an orbital platform shaker for 1 hour at 4° C. The resuspended PEG 8000 pellet is organically extracted by the addition of an equal volume of chloroform: isoamyl alcohol (24:1, v/v) with vigorous vortexing and then clarified by centrifugation at 4,000 g for 10 minutes at 20° C. The aqueous phase is reserved, the interface and organic phase are reextracted with a volume of TNE buffer equal to one third of the original sample volume and both aqueous phases are combined, yielding extracted PEG pellet.

6. In most cases, it is desirable to conduct at least one step of anion exchange chromatography after the second organic extraction. Extracted PEG pellet or extracted polymer pellet is subjected to ion exchange chromatography on a resin, gel or matrix with positive charge. Typical anion exchange matrices include, but are not limited to, DEAE cellulose DEAE agarose DEAE Biogel DEAE dextran DEAE Sephadex DEAE Sepharose Aminohexyl Sepharose Ecteola cellulose TEAE cellulose QAE cellulose mono-Q, or Benzoylated diethylaminoethyl cellulose.

The preferred anion exchanger is DEAE Sepharose CL-6B (Pharmacia). General background information on ion exchange chromatography can be found, for example, in E. A. Peterson, "Cellulosic Ion Exchangers" in Work, T. S. et al. *Laboratory Techniques in Biochemistry and Molecular Biology* Volume 2, Part II, pages 223 et seq. North-Holland 1970.

One predominant effect of anion exchange on the extracted PEG pellet is the removal of DNA. In principle, therefore, anion exchange can be substituted by the addition and removal of DNAse, or by alternative treatments designed to remove DNA at this stage of the purification process.

7. A final step of gel filtration chromatography follows anion exchange. Typically, Sepharose CL-4B (Pharmacia) is employed, but numerous other types of gel filtration matrices can be substituted. See, for example, Fischer, L., "Gel Filtration Chromatography," in Work, T. S. et al. *Laboratory Techniques in Biochemistry and Molecular Biology* Elsevier 1980.

While the particular sequence of chromatographic steps of anion exchange followed by gel filtration are the typical protocols for purifying HAV in this invention, it will be understood that the sequence can be varied. For example, gel filtration may precede anion exchange.

ADDITIONAL STEPS

Other conventional or known steps normally used in purification of virus proteins or virions may be added to the process of purifying HAV. These steps include, but are not limited to:

(a) selective adsorption or partition on a solid-phase, e.g. silica gel, calcium phosphate charcoal, or celite alumina;

(b) hydrophobic chromatography with, e.g. butyl agarose; and (c) selective extraction with other solvents or reagents.

(d) An additional precipitation is another step useful for isolating HAV. Other methods include (e) chromatography by any standard method, including thin-layer, gel, molecular sieve, molecular exclusion, ion-exchange, ligand affinity, immunoaffinity, by electrophoresis;

(f) solvent fractionation by two phase extractions, e.g. with PEG and dextran;

(g) dialysis, ultrafiltration, or diafiltration;

(h) density-gradient centrifugation;

(i) electrofocusing;

(j) freeze drying, lyophilization; or (k) crystallization;

(l) addition of protease inhibitors and/or chelating agents to buffer; or (m) substitution of one buffer with another.

This list is by no means exhaustive. Its order is not an indication of the preferred order of purification. It will be understood that a successful purification of HAV may include any, some, or all of steps (a)–(m).

Additional processing steps of conventional and well known character are or may be needed to prepare purified HAV for a vaccine. For example, treatment with formalin, sterile filtration and adsorption to carriers or adjuvants are the typical basic steps for preparing a formalin-inactivated vaccine. See, for example, Provost, P. J. et al. Proc. Soc. Exp. Biol. Med. 160, 213 (1979); Provost, P. J. et al. J. Med Virol. 19, 23 (1986). HAV can be inactivated by heat, pH changes, treatment with organic solvents, ultraviolet irradiation, or exposure to formalin. It will be understood that the scope of the present invention encompasses, in addition to the F strain of C326 of HAV, any other HAV strain whether or not attenuated. Attenuated strains may be isolated by serial passage through cells, animals, or by other methods. See, for example, Provost, P. J. et al. Proc. Soc. Exp. Biol. Med. 170, 8 (1982); and Provost, P. J. et al. J. Med. Virol. 20, 165 (1986), for details on attenuation. The purification methods of the present invention are readily and easily adaptable to attenuated or unattenuated strains.

In this invention, lower alkane contains 1–6 carbon atoms.

The example that follows illustrates the practice of the invention, but it is not intended to limit the scope and content of the invention.

EXAMPLE

Procedure for the Purification of Hepatitis A Virus (HAV) from MRC-5 Cells

A. Cell Disruption

MRC-5 cells infected with attenuated HAV (strain F of CR-326) were harvested by scraping and freezing at −70° C. in four roller bottle equivalents per tube. Two tubes were thawed by the addition of 3 mls of lysis buffer per tube (10 mM Tris-HCl pH 7.5, 10 mM NaCl, 1.5 mM $MgCl_2$) and by vigorous vortexing (10–15 seconds at setting 10 in a Vortex-Genie) and were then held on wet ice for 15 minutes. The lysates were twice frozen and thawed in an ethanol-dry ice bath and 37° C. water bath, and each tube was sonicated three times for 30 seconds at the maximum wattage output of a cup horn sonicator with a circulating ice water bath (Branson Sonifier Cell Disrupter 185 and Ultrasonics cup horn). The sonicates were pooled and assayed for protein using a Bradford protein assay (BioRad) with BSA (Bovine Serum Albumin) as a standard and then adjusted to 3 mg protein per ml in TNE buffer (10 mM Tris-HCl pH 7.5, 150 mM NaCl, 1 mM EDTA). The sonicate was organically extracted by the addition of an equal volume of methylene chloride: isoamyl alcohol (24:1, v/v) with vortexing for 1 minute and was centrifuged at 3,000 rpm for 10 minutes at 20° C. in an IEC centrifuge (~3,000 g) to achieve phase separation. The aqueous phase was reserved, the organic phase discarded and the interface was reextracted, with a volume of TNE buffer equal to one third of the original sample volume, by vortexing and centrifugation as before. The two aqueous phases were pooled and the volume measured, yielding Hepatitis A virus in organically extracted cell lysates.

B. Polyethylene glycol (PEG) precipitation

Hepatitis A virus in the organically extracted cell lysates was concentrated by polyethylene glycol precipitation (PEG). Lysates were adjusted to 500 mM NaCl and made 4% (w/v) in PEG 8000 by the addition, with vigorous vortexing, of 40% (w/v) PEG 8000 (prepared in 10 mM Tris-HCl pH 7.5, 500 mM NaCl, 1 mM EDTA). The 4% PEG lysates were held at 4° C. for 1 hour and then centrifuged at 1,500 g for 10 minutes at 4° C. in a Beckman HB-4 rotor. The supernatant was removed and the PEG pellet resuspended by vigorous vortexing in 10 mls of 10 mM Tris-HCl pH 7.5, 150 mM NaCl, 10 mM EDTA and by sonication 3 times for 30 seconds at maximum wattage output in a cup horn sonicator with a circulating ice water bath as described above. The sonicated, resuspended precipitate was then rotated at 200 rpm on an orbital platform shaker for 1 hour at 4° C. The resuspended PEG 8000 pellet was organically extracted by the addition of an equal volume of chloroform: isoamyl alcohol (24:1, v/v) with vigorous vortexing and then clarified by centrifugation at 4,000 g for 10 minutes at 20° C. The aqueous phase was reserved, the interface and organic phase were reextracted with a volume of TNE equal to one third of the resuspended PEG pellet volume and both aqueous phases were combined, yielding resuspended PEG pellet.

C. Ion exchange and Gel filtration chromatography

The resuspended PEG pellet was adjusted to 350 mM NaCl and chromatographed at a pump speed of 3 mls/minute over a 2 ml DEAE-Sepharose CL-6B (Pharmacia) column, prepared in Kontes Flex column (1.0×5.0 cm) and equilibrated in 10 mM Tris-HCl pH 7.5, 350 mM NaCl, 1 mM EDTA. The first 15 mls of eluate were collected and chromatographed through a Sepharose CL-4B (Pharmacia) column (2.6×95 cm), equilibrated in TNE buffer operated at pump speed of 20 ml/hour. Fractions of five mls were collected, yielding substantially purified, attenuated HAV. Fractions containing HAV were identified by HAVAG RIA (Abbot Laboratories), combined, made sterile by filtration through a Millex GV-0.22 µ filter (Millipore) and stored at 4° C. The concentration of HAV in the pool was determined by quantitative HAVAG RIA and the sample concentrated (if necessary) in an Amicon ultrafiltration cell fitted with a YM100 membrane.

With a sample of 5 µg purified HAV, SDS-polyacrylamide gel electrophoresis failed to detect any impurities after silver staining and Western blotting.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims.

We claim:

1. A method of purifying Hepatitis A virus such that only HAV specific proteins are visible on an SDS gel upon loading 5 micrograms or less of purified HAV and silver staining the gel, comprising the steps of (a) growing and harvesting cells infected with Hepatitis A virions;

(b) lysing the harvested cells by sonication;

(c) extracting the lysate with an organic:antifoaming agent mixture wherein the organic agent is selected from methylene chloride and chloroform and the antifoaming agent is isoamyl alcohol, the ratio of the organic agent to antifoaming agent is about 15:1 to about 50:1, and retaining the aqueous phase;

(d) concentrating the aqueous phase with sufficient polyethylene glycol effective to precipitate the Hepatitis A virions, wherein the polyethylene glycol has a molecular weight of between 2,000 daltons and about 12,000 daltons, said polyethylene glycol having a final concentration in the aqueous phase of between about 2% (w/v) and about 10% (w/v);

(e) extracting the precipitated Hepatitis A virions with an organic:antifoaming agent mixture wherein the organic agent is selected from methylene chloride and chloroform and the antifoaming agent is isoamyl alcohol and retaining the aqueous phase;

(f) subjecting the aqueous phase to ion exchange chromatography;

(g) gel filtering fractions containing Hepatitis A virions, yielding substantially purified Hepatitis A virions such that only HAV specific proteins are visible on an SDS gel upon loading 5 micrograms or less of purified HAV and silver staining the gel.

2. The method of claim 1 wherein the cells infected with Hepatitis A virions are MRC-5 cells.

3. The method of claim 2 wherein the Hepatitis A virions are the F strain of CR-326.

4. The method of claim 1 wherein the Hepatitis A virions are attenuated before the growing and harvesting of step (a).

5. The method of claim 1 wherein the polyethylene glycol has a molecular weight of about 8,000 daltons, said polyethylene glycol having a final concentration in the aqueous phase of about 4% (w/v).

6. A method of purifying Hepatitis A virus such that only HAV specific proteins are visible on an SDS gel upon loading 5 micrograms or less of purified HAV and silver staining the gel, comprising the steps of:

(a) growing and harvesting cells infected with Hepatitis A virions;

(b) lysing the harvested cells by sonication;

(c) extracting the lysate with an organic:antifoaming agent mixture wherein the organic is selected from methylene chloride and chloroform and the antifoaming agent is isoamyl alcohol, the ratio of the organic to antifoaming agent is about 15:1 to 50:1, and retaining the aqueous phase;

(d) concentrating the aqueous phase with sufficient polyethylene glycol, wherein the polyethylene glycol has a molecular weight of between 2,000 daltons and about 12,000 daltons, said polyethylene glycol having a final concentration in the aqueous phase of between about 2% (w/v) and about 10% (w/v), to precipitate the Hepatitis A virions;

(e) extracting the precipitated Hepatitis A virions with an organic: antifoaming agent mixture wherein the organic is selected from methylene chloride and chloroform and the antifoaming agent is isoamyl alcohol and retaining the aqueous phase;

(f) subjecting the aqueous phase to ion exchange chromatography on a resin, gel or matrix with a positive charge; and (g) gel filtering ion-exchange fractions containing Hepatitis A virions, yielding substantially purified Hepatitis A virion such that only HAV specific proteins are visible on an SDS gel upon loading 5 micrograms or less of purified HAV and silver staining the gel.

7. A process according to claim 6 wherein step (b) further includes freezing and thawing the cells prior to sonication.

* * * * *